United States Patent [19]

Apple et al.

[11] 4,263,428

[45] Apr. 21, 1981

[54] BIS-ANTHRACYCLINE NUCLEIC ACID FUNCTION INHIBITORS AND IMPROVED METHOD FOR ADMINISTERING THE SAME

[75] Inventors: Martin A. Apple, Daly City; C. Anthony Hunt, San Francisco, both of Calif.; Hiroaki Yanagisawa, Tokyo, Japan

[73] Assignee: The Regents of the University of California, Berkeley, Calif.

[21] Appl. No.: 13,433

[22] Filed: Feb. 23, 1979

Related U.S. Application Data

[63] Continuation-in-part of Ser. No. 889,853, Mar. 24, 1978, abandoned.

[51] Int. Cl.³ .................... C07H 17/08; A61K 31/70
[52] U.S. Cl. ................................. 536/17 A; 424/180
[58] Field of Search ................ 536/17, 17 A; 424/180

[56] References Cited

U.S. PATENT DOCUMENTS 4,112,217  9/1978  Henry et al. .................. 536/17 A

*Primary Examiner*—Johnnie R. Brown
*Assistant Examiner*—Blondel Hazel
*Attorney, Agent, or Firm*—Phillips, Moore, Weissenberger, Lempio & Majestic

[57] ABSTRACT

A new group of compounds having an enhanced ability to inhibit nucleic acid functions have been prepared. These drugs are bis-anthracyclines wherein two anthracycline molecules are linked through their C-13 carbon atoms by amino and/or hydroxy-dicarboxylic acids and their derivatives to form the bis-compounds. Such bis-anthracyclines may be even more effectively delivered to selected sites in a mammalian organism by incorporating the same within uniformly sized liposomes.

22 Claims, No Drawings

BIS-ANTHRACYCLINE NUCLEIC ACID FUNCTION INHIBITORS AND IMPROVED METHOD FOR ADMINISTERING THE SAME

This application is a Continuation-In-Part of application Ser. No. 889,853 filed Mar. 24, 1978, now abandoned.

BACKGROUND OF THE INVENTION

Anthracyclines are compounds previously isolated and studied and which have shown activity as bacterial antibiotics and anti-cancer agents in mammalian chemotherapy. Most such anthracyclines are natural products derived from the bacterial species, Actinomycetes and Streptomycetes. Generally, such anthracyclines have the structure:

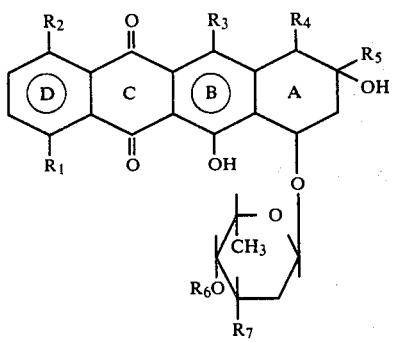

wherein $R_1$, $R_2$ and $R_3$ are usually —H, —OH or —OCH$_3$. The $R_6$ substituent is normally —H or a mono-or di-saccharide; while $R_7$ is, most often, —OH, or a simple -amine or alkylamine. The ring structure designated "A" has a wide variation in the $R_4$ and $R_5$ substituents. $R_4$ may range from —H to a-carboxyl ester; while $R_5$ may be —CH$_2$CH$_3$,

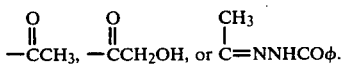

Where the $R_5$ substituent is —CH$_2$CH$_3$, the commercial products are known as Cinerubin or Aclacinomycin; where it is —COCH$_3$, the commercial products are known as Daunorubicin; where —COCH$_2$OH, as Adriamycin; and where a C=NNHCO$\phi$, as Rubidazone.

While many anthracyclines have been produced, most exhibit low effectiveness or potency against neoplasms, or produce unacceptable side effects. On the other hand, some anthracyclines, such as the aforementioned Daunorubicin and Adriamycin find clinical use in the treatment of various types of cancer. It appears that those anthracyclines in which $R_1$ is —H or sometimes OH are quite toxic compared to those with —OCH$_3$. Where $R_3$ is a methoxy group, the anti-cancer activity appears to be less than where $R_3$ is the hydroxy group. In addition, most anthracyclines produce accumulative toxicity to vital tissues such as bone marrow and heart. While over one hundred analogs are now known, most are less potent and less effective than the four or five clinically useful analogs.

It is theorized that the anthracyclines block the functions of the deoxyribonucleic acids (DNA) by insertion of their BCD aromatic ring region in between successive base pairs of the DNA structure. Thus it appears that the drug effectiveness relies upon the binding thereof to a site on the receptor DNA molecule and/or other receptor molecules. Some evidence suggests that the drug acts only so long as it is bound to the receptor site and is made inactive as soon as it dissociates therefrom. It also appears that if it were possible to assure that a greater number of closely related receptor sites were drug-occupied, effectiveness would be greatly enhanced. Unfortunately, there is a vanishingly small probability that two drug molecules ingested at the same time will arrive simultaneously at related receptor sites and both remain simultaneously bound thereto.

On the other hand, if either drug molecule is attached to a similar drug molecule, then as it arrives at the receptor area it will increase the chance of two-receptor interactions occurring at almost the same time by an enormous factor. The further chance that both will dissociate from their respective receptor sites at the identical moment is also greatly reduced. In addition, each time one part of the molecule begins to dissociate the attachment of the other part of the molecule will enhance the opportunity that the dissociating part will re-attach. It appears therefore that a drug with multiple receptor sites binding ability could potentially be much more potent and effective than a drug having only one receptor site binding structure. Although the drugs disclosed herein are anthracyclines, this principle has obvious application to other drug classes.

In addition to the ability to effectively attach to binding sites on the cell DNA, and other receptor molecules, drug effectiveness is very much related to its toxicity against the tissues of the disease-free or normal portions of the organism. It is therefore desirable to protect the normal portions of the organism from the drug, yet at the same time, effectively direct the drug specifically against the diseased tissues of the organism. Any means of selectively directing the drug to the diseased portions while bypassing the disease-free portions of the organism will greatly benefit the effectiveness of any therapeutic methods. In addition, such method should enable the use of lower dosages relative to the weight of the organism as a whole but, yet supplies sufficient drug at the diseased sites to produce a high level of activity against the diseased portions of the organism. Lower dosage rates combined with careful "targeting" of the drug to the diseased site will obviously greatly diminish undesired side effects to the organism.

It should be understood that while the theories expressed above may underlie the demonstrated effectiveness of the drug and treatment method disclosed hereinafter, its accuracy should in no way be taken to limit the fact that the bis-anthracyclines and liposome delivery method disclosed hereinafter truly demonstrate an improvement over previously known related drugs and methods.

BRIEF DESCRIPTION OF THE INVENTION

Improved anthracycline compounds have been prepared. These compounds show increased effectiveness against neoplasms. In addition, a method has been devised for increasing the specificity of action of said anthracyclines against neoplasms whereby the effective dosage rate may be greatly reduced and pervasion of the drug throughout the entire organism is minimized.

More specifically, the novel drugs of the invention comprise bis-anthracyclines wherein two anthracycline molecules are linked together to form a single molecular structure. The linkage units are derived from hydroxy-or amino-dicarboxylic acids. All known anthracyclines are susceptible to linkage into bis-compounds; however, for the purposes of the invention, those anthracyclines having a ketone substituent at the C-13 carbon atom are preferred as those linked to form improved drugs. Such bis-anthracycline compounds therefore generally have a structure such as the example that follows:

It is still another object of the invention to provide a method for delivering bis-anthracycline drugs to diseased sites in a highly effective manner.

It is yet another object of the invention to encapsulate bis-anthracycline drugs within liposomes.

It is still another object of the invention to provide a method for producing liposomes of uniform size.

It is yet another object of the invention to provide an extrusion method for producing liposomes of uniform size.

Other objects and advantages of the invention will become apparent from a review of the following disclosure and the claims appended hereto.

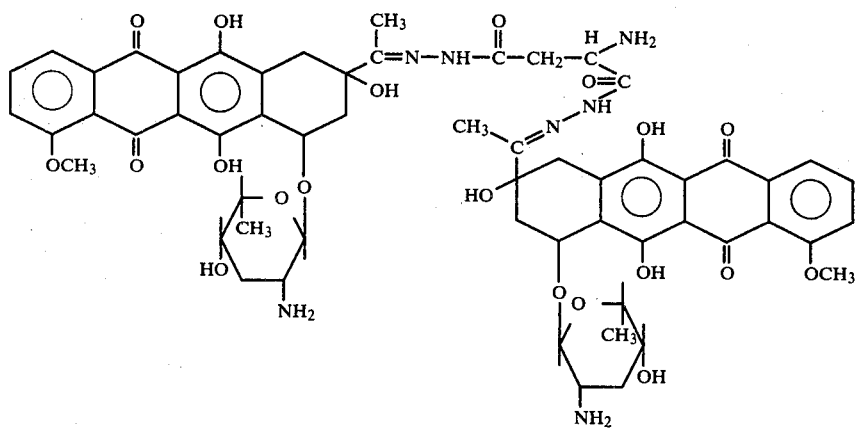

Since it is necessary that the C-13 carbon atom forms a part of a functional ketone grouping, it will be noted that the Daunorubicin, Adriamycin and Carminomycin anthracyclines and their analogs are greatly preferred for use in forming the bis-compounds. It should be understood however that event those anthracyclines which do not have ketone substituents on the C-13 carbon atom can be converted into suitable bis-compounds through the C-14 atom or so long as the particular substituent on the C-13 carbon atom is converted either to a ketone grouping prior to the linking step or to a suitable moiety for linkage to carboxylic groups.

While the bis-anthracyclines exhibit increased ability to interfere with DNA replication, their in vivo effectiveness can be even more greatly enhanced if the bis-anthracyclines are incorporated within liposomes before ingestion. More specifically, the bis-anthracyclines may be encapsulated within liposome structures which comprise minute hollow spheres of lipid compounds. These liposome structures are known in the prior art and are prepared from various types of lipids such as phospholipids, cholesterols etc. It is known that various materials including drugs may be encapsulated within the liposome interiors and it has been found that incorporating the bis-anthracyclines within such structures provide increased effectiveness of the drug within the mammalian organism.

It is therefore an object of the present invention to provide bis-anthracyclines.

It is another object of the invention to provide new compositions of matter where two anthracycline molecules are linked together to form useful bis-anthracycline drugs.

It is another object of the invention to provide a method for producing bis-anthracycline drugs.

DETAILED DESCRIPTION OF THE INVENTION

The present invention contemplates new compositions of matter known as bis-anthracyclines. Bis-anthracyclines are two anthracycline moieties linked together with a bridge structure generally derived from hydroxy-or amino-dicarboxylic acids.

For purposes of the invention the anthracyclines are linked together at the C-13 carbon atom position. More specifically, a typical anthracycline molecule may be depicted as:

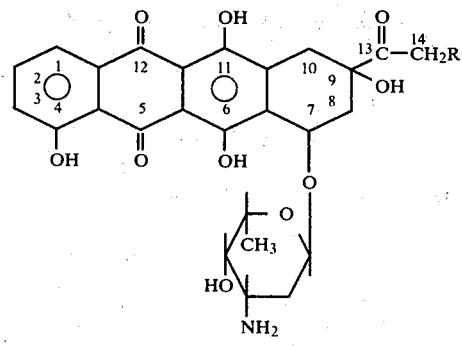

It should be noted that a ketone functional group, i.e.,

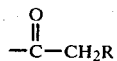

exists at the C-13 carbon position and R may be H, OH, O-alkyl, etc.

It has been determined that hydroxy- or amino-dicarboxylic acids will react with the C-13 carbon atoms to form a cross-linked bis-anthracycline compound. This reaction can occur under conditions sufficiently mild to leave the rest of the anthracycline molecule unchanged along with the usual characteristics thereof.

The bis-anthracyclines therefore generally have the structure:

vert them to the equivalent cross-linking agents previously noted.

In any event, the mono-anthracyclines may be cross-linked to form the bis-anthracyclines, either in acid medium or in basic medium. When reacted in acid medium, the straight chain linked bis-anthracyclines result. When reacted in neutral or basic medium, (or when the straight-chain product is further reacted in basic me-

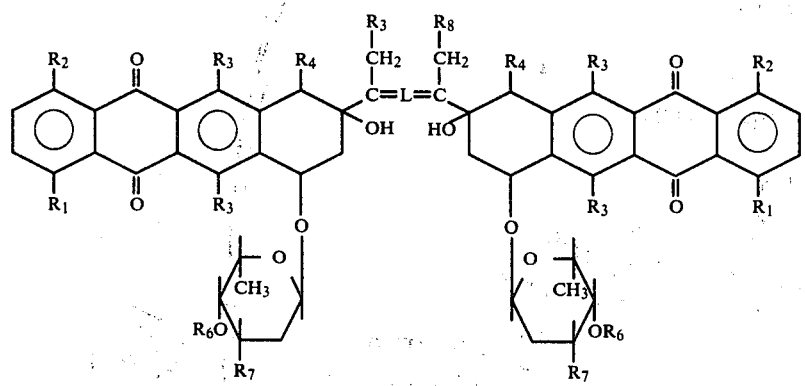

wherein $R_1$ is usually OH or $OCH_3$; and $R_2$ and $R_3$ are usually —H, —$OH_2$ or —$OCH_3$; $R_4$ may range from —H to a carboxyl ester; $R_6$ may be —H or a mono- or di-saccharide; and $R_7$ is, most often, —OH or an amine or mono or di-alkylamine, and $R_8$ is —H, —OH or -O-ester.

L can be an hydroxy- or amino-dicarboxylic acid derivative. More specifically, L may be an amino-dicarboxylic acid dihydrazide:

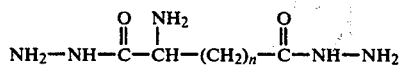

wherein n=1 to 4; and the linking substituent then is:

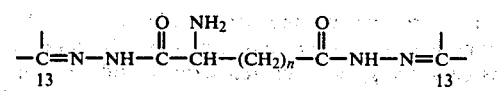

wherein the C-13 carbon at each end indicate the bis-linkage on two anthracycline molecules and the C-N may or may not be saturated or substituted.

In addition, amino-diesters may be utilized as a cross-linking agent. For instance ROCOCH($NH_2$)($CH_2$)$_n$COOR (wherein R=$CH_3$, —$C_2H_5$, etc.) may serve as a cross-linking agent. It is only necessary to react such esters with hydrazine prior to the linking step to condium) the straight-chain linking substituent is converted to the cyclic structure:

$$\underset{13}{-C}\underset{NH-NH}{\overset{NH-CH-(CH_2)_n-CHR-C-NH-N=C-}{\diagup\diagdown\diagup}}\underset{O}{\overset{\|}{13}}$$

, NON-RING REGION wherein R=H or any suitable moiety.

Some studies have indicated that the cyclic linked bis-anthracyclines may exhibit greater activity than their straight-chain counterparts. For example, they are over 10 times as potent as inhibitors of DNA directed transcription as the noncyclic straight chain counterpart. For purposes of reference herein, the bis-anthracyclines having straight-chain linking will be referred to as Type I; while those having the cyclic linkage will be referred to as Type II.

A great variety of hydroxy- and amino-dicarboxylic acids (and esters) may be utilized as cross-linking agents. A number of such variations are noted in Tables 1, 1a and 1b herein below. However, other variations are possible and it is not intended to limit the linkage to those noted in Tables 1, 1a and 1b.

The preparation of the bis-anthracyclines from the mono-anthracyclines may be schematically noted as follows:

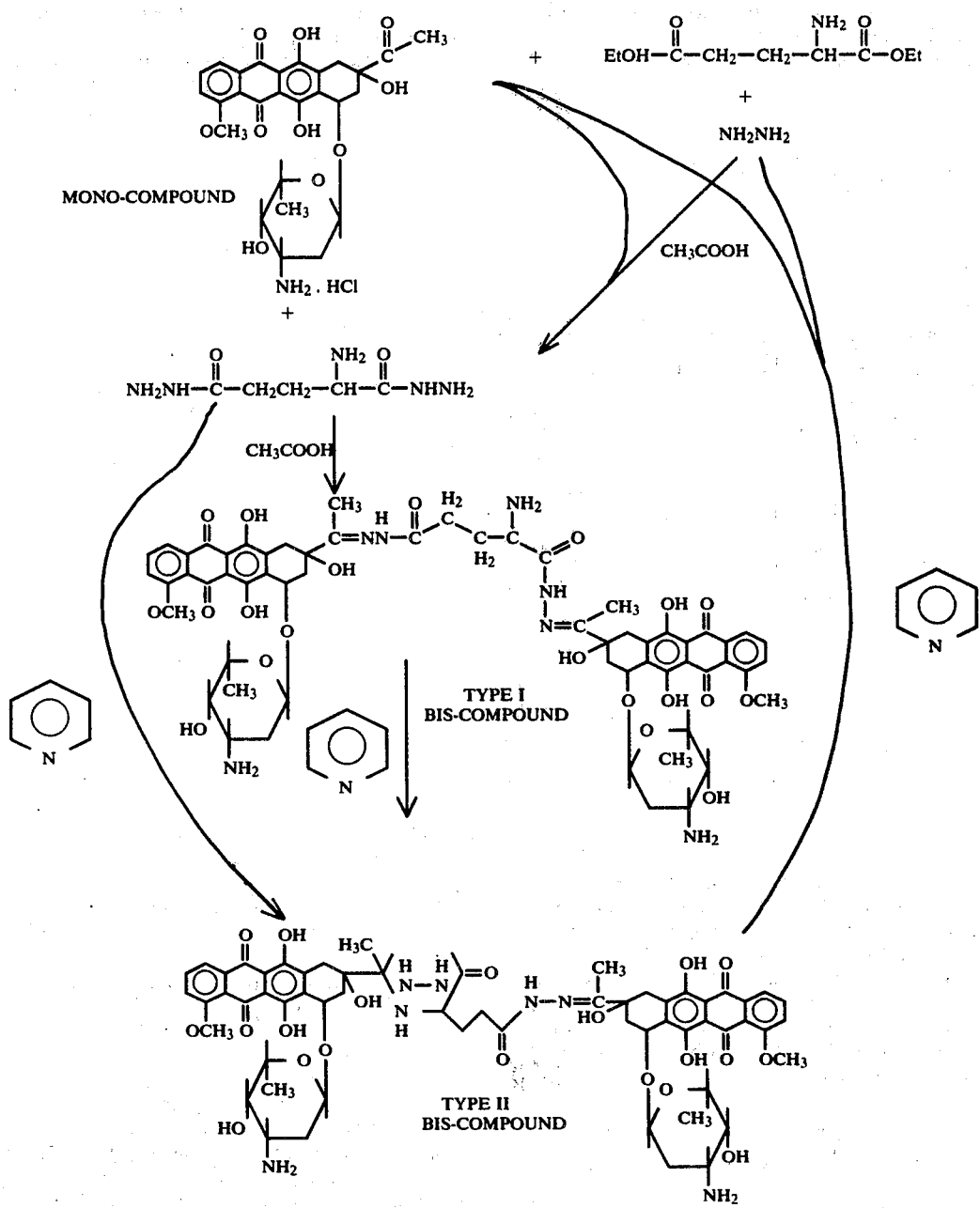

As noted above, to yield the straight-chain linked or Type I bis-anthracycline, the mono-anthracycline is reacted with the cross-linking agent in an acid medium, e.g., acetic acid. To yield the cyclic linked Type II bis-anthracycline, the mono-anthracycline is reacted in a neutral or basic medium, e.g., amines, pyridines, etc.

The type I product may also be converted to the Type II product by contacting the initial Type I product with a basic medium. Conversions to the Type II product take place almost completely.

Reaction conditions are extremely mild so that conversion to the bis-compounds does not degrade or affect the basic anthracycline structure. Particular care must be taken to protect the saccharide substituents that occur on many of the anthracyclines. In general, the cross-linking agent is reacted with the mono-anthracycline in a 1:2 molar ratio in an alcohol (MeOH) medium at about 25° C. If the Type I bis-compound is desired, a suitable acid, e.g., acetic, is added to the reaction mixture. If the Type II bis-compound is desired the reaction is conducted in neutral media or a suitable base, e.g., pyridine, is added.

The reaction is permitted to proceed slowly for a period of hours to days, its progress being followed by TLC and standard analysis techniques to determine the conversion of the mono-anthracycline to the bis-anthracycline. The bis-compound either precipitates from the reaction solution or is recovered therefrom by standard Bis-daunorubicin linked by straight chain of D-glutamic dihydrazide was prepared as per the following:

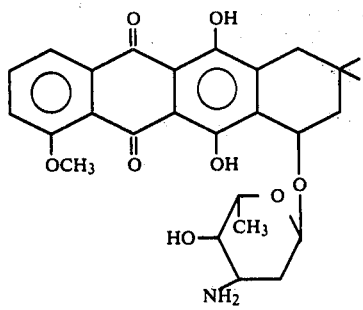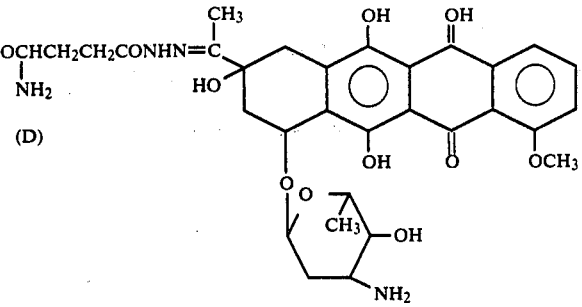

(D)

methods. Yields are in the 90% range.

The following examples demonstrate the preparation of the bis-anthracyclines. Both the preparation of Type I straight-chain linked product and Type II cyclic linked product are illustrated.

In all instances, conversion to the bis-compound was monitored by TLC conducted on a pre-coated silica gel plate supplied by E. Merck (F-254, thickness 0.25 mm) utilizing a solvent system of $CHCl_3$-MeOH-AcOH-$H_2O$ (80:20:14:6)

TLC was conducted on a pre-coated silica gel plate of E. Merck (F-254, thickness 0.25 mm)) with a solvent system of $CHCl_3$-MeOH-AcOH-$H_2O$ (80:20:14:6)

EXAMPLE 1

A solution of 56 mg (0.1 mmol) of daunorubicin hydrochloride and 9 mg (0.05 mmol) of D-glutamic dihydrazide in 5 ml of methanol and 0.3 ml of acetic acid was kept at room temperature overnight. To the solution was added a large volume of ether and the precipitates were collected by filtration. The precipitates were dissolved in 5 ml of methanol and 0.4 ml of 0.5 N HCl-methanol and ether was added to the solution. The precipitates of the bis-daunorubicin hydrochloride were collected by filtration. Amorphous powder; yield 62 mg; mp 182° (dec); TLC, Rf 0.05.

EXAMPLE 2

Bis-daunorubicin linked by cyclic chain of D-glutamic dihydrazide was prepared as follows:

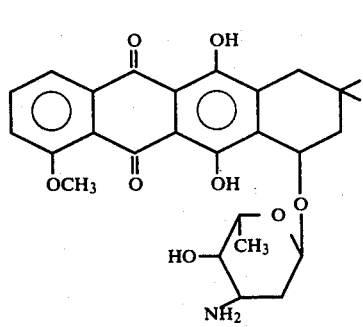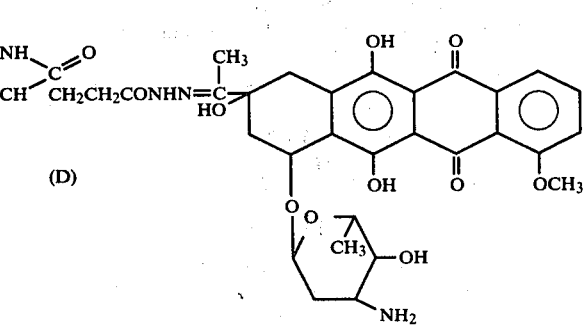

(D)

Bis-daunorubicin linked by D-glutamic dihydrazide

D-Glutamic dihydrazide was first prepared for use as the linking moiety by the following reaction:

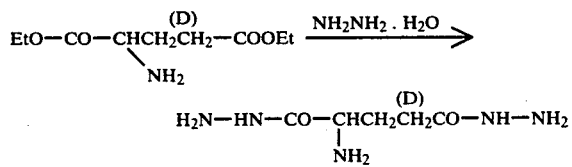

To a solution of 1.015 g of diethyl D-glutamate in 5 ml of methanol was added a solution of 550 mg of hydrazine hydrate in 3 ml of methanol and the mixture was stirred at room temperature overnight. The reaction mixture was concentrated in vacuo and the residue was crystallized in a small amount of ethanol-ether. Recrystallization from methanol. Mp 150°–151° (dec), $[\alpha]_D^{27} -27.2°$ (c0.5, $H_2O$).

A solution of 56 mg (0.1 mmol) of daunorubicin hydrochloride and 9 mg (0.05 mmol) of D-glutamic dihydrazide in 5 ml of methanol was stirred at room temperature for 9 days. Ether was added to the reaction mixture and the preciptates were collected by filtration. The precipitates were dissolved in 5 ml of methanol and 0.3 ml of acetic acid and then ether was added to the solution. The precipitates of the bis-daunorubicin acetate were collected by filtration. Amorphous powder; yield 60 mg; mp 192° (dec); TLC,Rf 0.35.

EXAMPLE 3

Bis-daunorubicin of L-glutamic dihydrazide was prepared as follows:

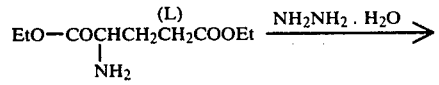

-continued $$H_2NHNCOCHCH_2CH_2CONHNH_2 \quad (L)$$
$$| \atop NH_2$$

The L-Glutamic dihydrazide was prepared by the same procedure as in the synthesis of D-glutamic dihydrazide. Mp 149°–150° (dec); $[\alpha]_D^{27}$ 26.0 (c0.5, H$_2$O).

Bis-daunorubicin linked by straight chain of L-glutamic dihydrazide preparation.

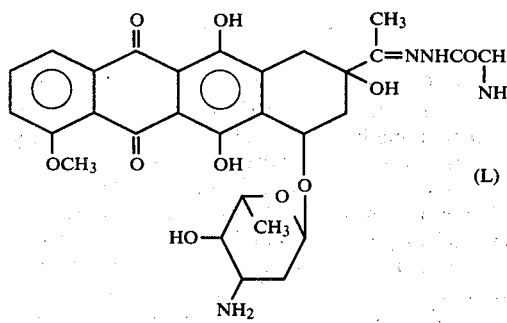

A solution of 56 mg (0.1) mmol) of daunorubicin hydrochloride and 9 mg (0.05 mmol) of L-glutamic dihydrazide in 5 ml of methanol and 0.3 ml of acetic acid was maintained at room temperature overnight. To the reaction solution was added ether and the precipitates were collected by filtration. The precipitates were dissolved in 5 ml of methanol and 0.4 ml of 0.5 N HCl-methanol.Ether was then added to the solution. The precipitates of the bis-daunorubicin hydrochloride were collected by filtration. Amorrphous powder; yield 62 mg; mp 179° (dec); TLC, Rf 0.05.

EXAMPLE 4

Bis-daunorubicin linked by cyclic chain of L-glutamic dihydrazide

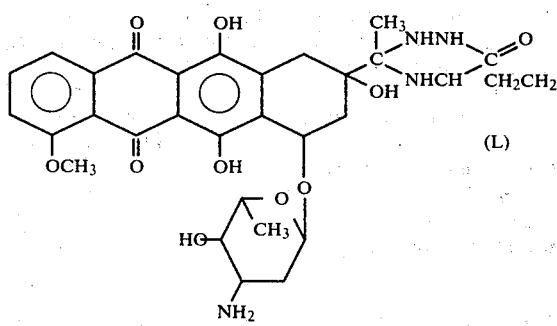

A mixture of 56 mg (0.1 mmol) of daunorubicin hydrochloride and 9 mg (0.05 mmol) of L-glutamic dihy-drazide in 5 ml of methanol was stirred at room temperature for 9 days. To the reaction solution was added ether and the precipitates were collected by filtration. The precipitates were dissolved in 5 ml of methanol and 0.3 ml of acetic acid. Ether was then added to the solution. The precipitates of the bis-daunorubicin acetate were collected by filtration. Amorphous powder; yield 60 mg; mp 192° (dec); TLC, Rf 0.35.

EXAMPLE 5

Bis-daunorubicin of L-aspartic dihydrazide preparation.

L-Aspartic dihydrazide was first prepared.

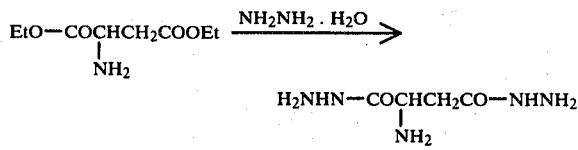

L-Aspartic dihydrazide was prepared by the same procedure as for the synthesis of D-glutamic dihydrazide noted above. Recrystallization took place from aqueous ethanol. Mp 165°–167° (dec).

Bis-daunorubicin linked by straight chain of L-aspartic dihydrazide preparation.

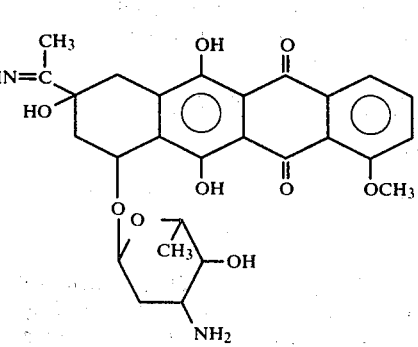

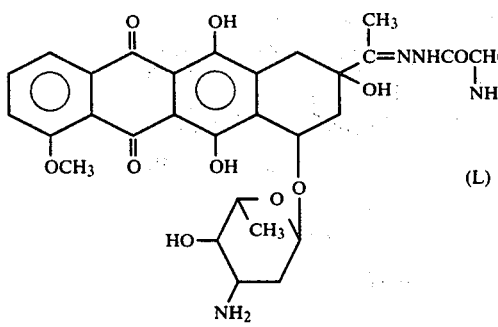
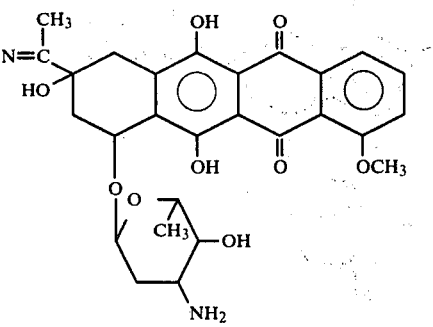

(L)

A solution of 56 mg (0.1 mmol) of daunorubicin hydrochloride and 8 mg (0.05 mmol) of L-aspartic dihydrazide in 5 ml of methanol and 0.3 ml of acetic acid was maintained at room temperature overnight. To the reaction solution was added ether and the precipitates were collected by filtration. The precipitates were dissolved in 5 ml of methanol and 0.4 ml of 0.5 N HCl-methanol. Ether was then added to the solution. The precipitates of the bis-daunorubicin hydrochloride were collected by filtration. Amorphous powder; yield 60 mg; mp 190° (dec); TLC, Rf 0.04.

A mixture of 56 mg (0.1 mmol) of daunorubicin hydrochloride and 8 mg (0.05 mmol) of L-aspartic dihydrazide in 5 ml of methanol was stirred at room temperature for 9 days. To the reaction mixture was added ether and the precipitates were collected by filtration. The precipitates were dissolved in 5 ml of methanol and 0.3 ml of acetic acid. Ether was then added to the solution. The precipitates of the bis-daunorubicin acetate were collected by filtration. Amorphous powder; yield 59 mg; mp 195° (dec); TLC, Rf 0.35.

EXAMPLE 6

Bis-daunorubicin linked by cyclic chain of L-aspartic dihydrazide preparation.

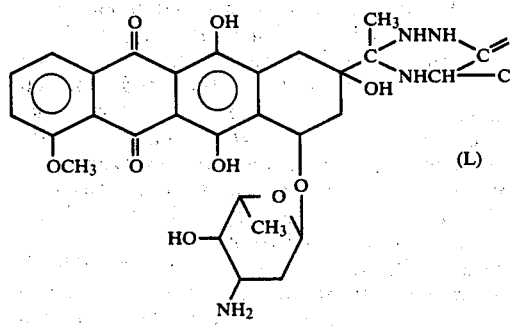
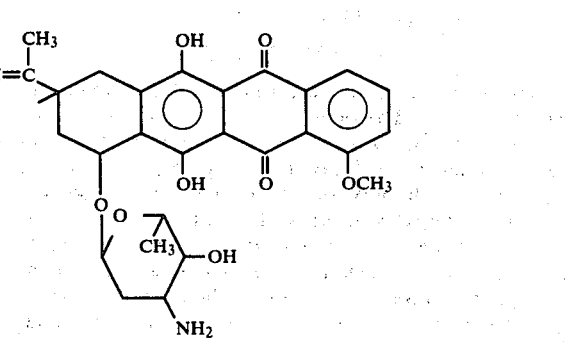

(L)

EXAMPLE 7

Conversion of straight chained bis-daunorubicin of D-glutamic dihydrazide to cyclic chained bis-daunorubicin

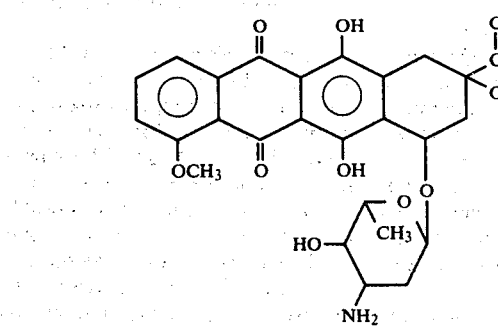
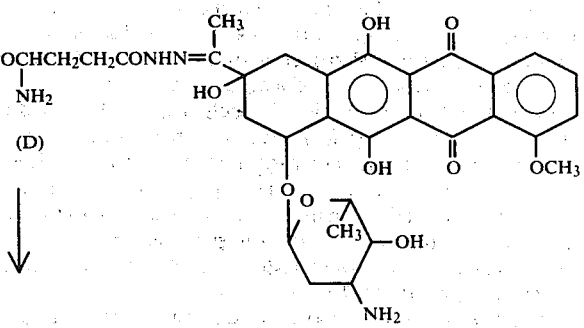

(D)

↓

-continued

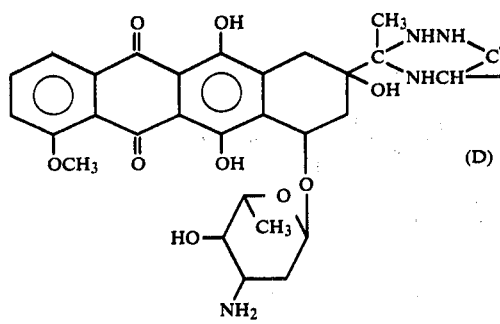
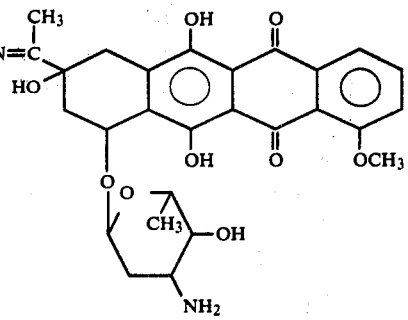

(D)

A solution of 20 mg of bis-daunorubicin linked by straight chain D-glutamic dihydrazide and 0.1 ml of pyridine in 3 ml of methanol was kept at room temperature for 7 days. Ether was added and the precipitates were collected by filtration. The precipitates were dissolved in 2 ml of methanol and 0.2 ml of acetic acid. Addition of ether gave the precipitates of the bis-daunorubicin linked by a cyclic chain of D-glutamic dihydrazide. Yield 15 mg.

Other bis-daunorubicins linked by straight chain moieties were prepared using the methods of the invention as noted above. These bis-daunorubicins and their activities are set forth in Table 6 below.

In any event, the crystallized bis-anthracyclines are recovered and kept refrigerated and protected from light until use. There is some tendency for some of the bis-compounds to very slowly degrade with time in solution and it is therefore advisable to use them as soon as possible unless they are stored as an anhydrous powder or protected as noted.

THE LIPOSOMES

Liposomes are lipid micro-vesicles of approximately spherical shape. The outer shell of a liposome consists of a phospholipid bilayer which encloses a volume of water, an aqueous solution or partly aqueous solution. Liposomes with only one lipid shell are designated unilamellar vesicles; those with additional lipid shells, like layers of an onion, are called multilamellar vesicles. Either type may be small, e.g., 150-400 nm in diameter, or large, e.g., up to the size of red blood cells. A large liposome may contain many times the volume of a small liposome.

Liposomes may be produced by hydration and mechanical dispersion of dried lipoidal material in an aqueous solution. The lipoidal material can be phospholipids or other lipids, cholesterol and its derivatives or a variety of amphiphiles including macromolecules or mixtures of these. However, liposomes prepared this way are mixtures of all the types noted above, with a variety of dimensions, compositions and behaviors. This unpredictable variety leads to inconsistent measures of liposome properties and unreliable characterizations. To reduce the heterogeneity of mechanically dispersed liposomes, such dispersions may be exposed to sonication which decreases average liposome size. Under extensive sonication, occasionally populations of liposomes are reduced to small unilamellar vesicles, but the sonic process does not give homogeneous dispersions of larger vesicles and can degrade the complex lipids and other components of the liposomes.

The preparation of liposomes and their use in drug therapy has been previously described. See, for instance, U.S. Pat. No. 4,053,585; German Pat. No. 2,532,317; Netherlands application No. 73/04133; and Biochemistry 16(12)2806(1977).

The present invention utilizes a process for producing liposomes of uniform size and composition; and with predictable properties. Such process utilizes extrusion as the final step during the production of the liposomes. The extrusion step may be repeated a number of times to further refine the liposomes with respect to decreasing their size and maximizing uniformity in size.

According to the invention the liposomes, in which the bis-anthracyclines are encapsulated are produced as follows:

Those agents which are to compose the lipid membrane of the liposome, such as phospholipids, cholesterol and/or other biologically active or inactive amphiphiles, or macromolecules are mixed in an organic solvent such as ethers, chloroform, alcohol, etc. and then dried onto the interior surface of a vessel under a vacuum. As an example, phosphatidic acid, L-alpha-lecithin and cholesterol were mixed into a chloroform: isopropanol: methanol::7:3:1 solution and vacuum dried. An aqueous solution of the drug was added to the dried lipids at a temperature above the phasse transition temperature of the lipid mixture. In this example, a bis-anthracycline at 1 mg/ml in isotonic phosphate buffer was added and the solution rolled with the lipids for one hour to allow slow hydration.

The resulting liposome size was greater than 0.5 micron in diameter (light scattering method). These mechanically dispersed liposomes are then passed through a Nuclear-Pore type filter (uniform pore size) starting with 1.00 micron and going successively down to the desired vesicle size (e.g., 0.1 micron). If the lipid concentration of these mechanically dispersed liposomes was greater than 10 mgm/ml the process was repeated for maximum uniformity. Following these steps the untrapped drug was removed from the vesicles by dialysis and the drug containing vesicles were collected for further use.

If the liposome size is desired to be less than 0.1 to 0.05 micron, the mechanically dispersed liposomes are then extruded under high pressure through a small orifice. For example, the mechanically dispersed liposomes were extruded using a French Press and Pressure Cell (Aminco type) maintained at about 17,000 psi during the entire extrusion. The extrusion may be repeated for enhanced uniformity of liposome. The extrusion pressure, orifice size, and temperature can be used to control the size of the resulting vesicles and very uniform liposomes can be easily and reproducibly made by this process.

Subsequent to the extrusion, the free untrapped drug can be removed readily by dialysis leaving a uniform, stable liposome population containing the drug.

As noted the liposome wall material may be any desired lipid, such as phospholipids, cholesterol, etc. Such liposomes may be produced, as noted, in closely controlled sizes; and, in addition, depending on the lipid employed, with positive or negative charges thereon.

Utilizing controlled liposome size, material and charge, it has been determined that in the mammalian organism, the liposomes will preferentially collect in particular organs, such as lung, liver, spleen, etc. Thus, the encapsulated drug may be delivered to specific sites within the organism. It will be apparent that utilization of the liposomes for such purposes, facilitates the effectiveness of the drug in contacting tissues at selected sites since the drug will concentrate at the selected sites. At the same time, the drug concentration throughout the general body tissues will be greatly lowered to reduce undesirable side effects.

INHIBITION OF DNA REPLICATION

Some bis-anthracyclines of the invention were tested for effectiveness in interfering with DNA replication or transcription reactions. For comparison, the clinically useful anthracycline Daunorubicin was used as the control and the bis-anthracyclines were prepared from the Daunorubicin monomolecules, utilizing various aminodicarboxylic acid linking agents. All of the bis-anthracyclines were produced under acid conditions to yield the Type I bis-anthracycline products as previously noted.

Drugs which bind to DNA as a receptor can inhibit a variety of replication or transcription reactions. One index of activity is the $I_{50}$ or concentration of drug in millimicromoles/milliliter in vitro needed to inhibit a nucleic acid-dependent function (the lower the $I_{50}$ the higher the activity of the drug. Tables 1, 1a, and 1b compare the activities of representative samples of bis-anthracyclines as inhibitors of RNA-directed-DNA polymerase (Apple, Ann. Rep. Med. Chem. 8:251, 1973, described the assay method used to determine activities, $I_{50}$.)

TABLE I
EFFECT OF BIS-ANTHRACYCLINES ON DNA TRANSCRIPTION IN VITRO

| LINKAGE GROUP | TYPE I PRODUCT mp C. | $I_{50}$ |
|---|---|---|
| 1. DAUNORUBICIN (control mono drug) | — | 105 |
| 2. NH₂NHCCH₂CHCH₂CNHNH₂ (O, OH, O) | 189 | 15 |
| 3. NH₂NHCCH₂CHCH₂CNHNH₂ (O, NH₂, O) | 182 | 10 |
| 4. NH₂NHCCH₂CHCNHNH₂ (O, NH₂, O) | 190 | 10 |
| 5. NH₂NHCCH₂NHCH₂CNHNH₂ (O, O) | 185 | 20 |
| 6. NH₂NHC—N—CNHNH₂ (ring) | 220 | 8 |
| 7. NH₂NHCCHOHCHOHCNHNH₂ (O, O) | 164 | 11 |

TABLE I-continued
EFFECT OF BIS-ANTHRACYCLINES ON DNA TRANSCRIPTION IN VITRO

| LINKAGE GROUP | TYPE I PRODUCT mp C. | $I_{50}$ |
|---|---|---|
| 8. NH₂NHCCHNH₂(CH₂)₃CHNH₂CNHNH₂ (O, O) | 190 | 5 |

TABLE 1a
ACTIVITY OF TYPE I BIS-ANTHRACYCLINES ON RSV RNA DEPENDENT DNA POLYMERASE.

| Linkage (only the asymmetrical portion of the linkage is noted) | MP °C. (dec) (HCl salt) | TLC Rf | $I_{50}$ μm/l |
|---|---|---|---|
| Daunorubicin (control) | | 0.59 | 105 |
| 1 CH₂CH₂ | 158 | 0.22 | 52 |
| 2 CH₂CH(OH)CH₂ | 189 | 0.14 | 15 |
| 3 CH₂CH(NH₂)CH₂ | 182 | 0.05 | 10 |
| 4 CH(NH₂) | 184 | 0.05 | 7.5 |
| 5 CH(NH₂)CH₂ (L) | 190 | 0.04 | 10 |
| 6 CH(NH₂)CH₂ (DL) | 180 | 0.04 | 7.5 |
| 7 CH(NH₂)CH₂CH₂ (L) | 179 | 0.05 | 7.5 |
| 8 CH(NH₂)CH₂CH₂ (D) | 182 | 0.05 | 7 |
| 9 CH(NH₂)(CH₂)₃(CH(NH₂) (DL) | 190 | 0.00 | 5.5 |
| 10 CHNHCH₂ | 185 | 0.03 | 20 |
| 11 (ring structure) | 220 | 0.07 | 8 |
| 12 (ring structure) | 183 | 0.05 | 8 |
| 13 CH(OH)CH(OH) (D) | 164 | 0.12 | 11 |
| 14 CH(OH)CH(OH) (L) | 164 | 0.12 | 9.5 |

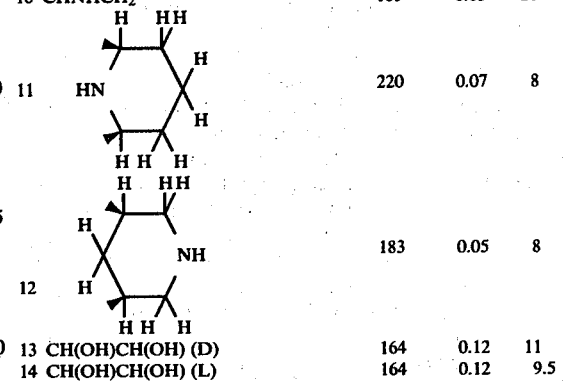

TABLE 1b
ACTIVITY OF TYPE II BIS-ANTHRACYCLINES ON RSV RAN DEPENDENT DNA POLYMERASE

| Linkage (only the non-ring portion of the linkage is noted) | MP °C. (dec) (acetate salt) | TLC Rf | $I_{50}$ μm/l |
|---|---|---|---|
| 1 CH₂ (L) | 195 | 0.35 | 3 |
| 2 CH₂CH₂ (L) | 195 | 0.35 | 2.5 |
| 3 CH₂CH₂ (D) | 192 | 0.35 | 2.5 |

From the above data, it is quite apparent that the bis-anthracyclines have tremendously enhanced ability to interfere with DNA replication as compared to one of the most highly active anthracyclines.

Activity of Straight Chain and Ring Linked Bis-anthracyclines

It appears that bis-anthracyclines produced in basic medium (Type II) are generally more potent than the corresponding bis-anthracyclines produced in acid medium (Type I), and that depending on the individual linkage group employed, either the D- or the L- isomer may be more activity as a drug, or they may be similar. Table 2 below presents a comparison:

TABLE 2

COMPARISON OF D/L AND FREE/RING BOUND AMINO LINKAGE GROUPS USING AMINO-DICARBOXYLIC ACID LINKAGE UNIT OF $$H_2NNH-\overset{O}{\underset{\|}{C}}-CH(NH_2)(CH_2)_2-\overset{O}{\underset{\|}{C}}-NHNH_2$$

| | TYPE I | | TYPE II | |
|---|---|---|---|---|
| isomer | mp (HCl)°C. | I$_{50}$ | mp (HCl)°C. | I$_{50}$ |
| L- | 179 | 8 | 195 | 2 |
| D- | 182 | 7 | 192 | <1 (a) |
| Daunorubicin - Control 150 | | | | |

(a) See Table 3

Table 2 tends to indicate that both the D- and L-forms of the bis-anthracyclines are similarly active as inhibitors of DNA transcription, but that the Type II compounds are significantly more active by almost an order of magnitude than the Type I compounds.

A study of the effectiveness of Type I and Type II bis-anthracyclines in vivo as anti-cancer drugs was also undertaken. Using a standard set of conditions such as that used by the National Cancer Institute, DBF$_1$ or CDF$_1$ mice with implanted P388 leukemia will usually succumb of cancer in 10–12 days. Drugs with clinical potential as cancer chemotherapeutics and used from Day 1 (day after leukemia implant) through Day 9 will extend the lifespan of these mice by 25% or more. Drugs which extend the life of these mice by 50+% are often superior, and drugs which extend the mouse lifespan under these conditions by 100+% are exceptional. Occasionally, a more advanced idsease model is used, in which the drug is given Q4D-5,9,13. In this model ("advanced P388") the first drug injection is delayed until 5–6 days before the expected death of the leukemic animal. The degree of effect is much less and many useful drugs which would pass the 25% increase in lifespan test when treatment is started on Day 1 would not show any effect on the advanced P388 leukemia treatment schedule. While it is more rigorous, some drugs do manage a 25+% increase in lifespan in the advanced P388. Many drugs clinically useful in cancer do not do this well in the advanced P388. The results indicate that the bis-anthracyclines herein are significantly active in the advanced P388 model. Table 3 shows these results:

TABLE 3

IN VIVO EFFECT OF BIS-ANTHRACYCLINES IN ADVANCED P388 LEUKEMIA

| COMPOUND HCl salt | % INCREASED LIFESPAN (Starting day 1) | % INCREASED LIFESPAN advanced P388 |
|---|---|---|
| Daunorubicin 1 | 65% | 30% |
| Table 1 | | |
| Compound #3 | 105% | 40% |
| 7 | — | 50% |
| 6 | — | 55% |
| 8* | — | 85% |
| Table 2 | | |
| Compound (a) | — | 50% |

*the acetate salt of compound 8 gave 50+% increased lifespan in advanced P388

Enhanced effectiveness of Bis-anthracyclines in Liposomes vs free bis-anthracyclines The new bis-anthracyclines are generally more effective against mouse cancer than the parent mono-anthracycline, such as Daunorubicin, and effective clinical mono-anthracycline (see Table 2). On the other hand, the bis-anthracyclines were less potent and less effective than would be expected when extrapolated from the comparison in Table 2 in which the bis-anthracycline was over 100 times as potent as Daunorubicin. If this discrepancy is as due to the lower transport of the very large bis-anthracycline molecule into cells or to the target cellular receptor, then overcoming this possible barrier should enhance the drug effectiveness of bis-anthracyclines.

Daunorubicin and Type I and/or Type II bis-anthracyclines were encapsulated in liposomes of the small unilamellar class, composed of phosphatidic acid, L-alpha lecithins, and cholesterol. These uniform small unilamellar vesicles were prepared by a final step of extrusion from a French Press at 17,000 lb/in$^2$ pressure.

The liposome encapsulated Type II bis-anthracycline drugs and free drugs were compared for their capacity to kill leukemic cells. The free drugs were about equally active and equally potent when Daunorubicin and the bis-anthracyclines (cited on page 15, D-isomer) were compared for their cell kill of L1210 leukemia cells. Daunorubicin was found to change only a few % (not significantly) between acting as a free drug or being liposome encapsulated (the I$_{50}$ was about 0.20 micromolar in both cases. However, the encapsulated bis-anthracycline (cited on Table 2, D-isomer) was very much improved in antileukemic activity when liposome encapsulated as noted in Table 4:

TABLE 4

IMPROVED ACTIVITY OF LIPOSOME ENCAPSULATED BIS-ANTHRACYCLINES

| STATE | I$_{50}$ LEUKEMIC CELL KILL |
|---|---|
| Free Drug | 0.250 micromolar |
| Liposome encapsulated | 0.003 micromolar |

In addition, Daunorubicin or bis-daunorubicin incorporated into these same liposomes and administered into BDF$_1$ mice carrying P-388 leukemia, could be given at more than 2 times the lethal dose of the free drug without producing a lethal effect. Under these conditions they were still effective anti-leukemic drugs in vivo, showing that such encapsulation produced a therapeutic advantage in making the doses less toxic. Whereas the therapeutically effective injected dose of the Type II bis-anthracyclines in treating murine leukemia may be 10–50 mg/kg on a q 4 d schedule, when the bis-anthracycline is incorporated into these same phosphatidic acid-lecithins- cholesterol liposomes, it is 2 to 8 mg/kg or 5 fold less. Thus it has been observed that the same liposome that lowers the risk of anthracycline toxicity can enhance the potency of the bis-anthracyclines. The combination of these effects, increasing the dose needed to produce toxicity and increasing potency or lowering the dose required to achieve a therapeutically useful effect in treating in vivo murine leukemia, is called enhancing the therapeutic index of a drug. We have thus seen that incorporation into liposomes enhances or improves the therapeutic index of both mono anthracyclines, such as those now used for treating human diseases, and the new bis-anthracyclines.

The bis-anthracyclines as disclosed above may be administered for therapeutic purposes in any of the commonly acceptable forms. The addition salts are especially useful. The hydrochloride, sulfate, acetate, phosphate, maleate forms are all producable. For the Type I and Type II compounds listed hereinbefore, all these salts are active as drugs in mice; but the organic acid salts were often less active than inorganic acid salts. However, other physiologically acceptable salts and variations thereof are contemplated for use herein. It is only necessary to ensure that any of the various forms of the compounds are acceptable from the pharmacological standpoint.

The bis-anthracyclines, whether in original or salt form, alone or encapsulated in liposomes, are introduced into the organism by any previously known method. When incorporated into liposomes, the drugs may be administered by intravenous or intraperitoneal injection, or orally, if desired. When administered without the liposomes, oral introduction is precluded, as the digestive process will destroy the drug before it can cross the intestinal membranes. Thus the drugs, in this instance, may be administered by injection. However, administration of the above noted drugs orally in effective doses, due to their incorporation into liposomes, offers a decided advantage over the requirement for drug injection with all its attendant risks and discomforts.

Directing drugs to specific or selective tissues in the mammalian species through incorporation in liposomes has been demonstrated. Table 5 below presents data in this regard and illustrates the effect of liposome size upon concentration in various tissues.

TABLE 5

| | % Dose[a] in Selected Tissues at Various Times after IV Administration of Size I and Size II[b] Liposomes to Mice | | | | | |
|---|---|---|---|---|---|---|
| | TISSUE | | | | | |
| TIME | LIVER | | SPLEEN | | LUNG | |
| HOURS | Size I | Size II | Size I | Size II | Size I | Size II |
| after 1 | 19.8 | 24.1 | 4.5 | 5.0 | 8.5 | 1.0 |
| after 5 | 8.3 | 20.5 | 2.9 | 2.7 | 5.7 | 0.5 |
| after 24 | 0.5 | 0.7 | 0.3 | 0.3 | 5.2 | 0.1 |

[a]The drug used was cytosine arabinoside. The liposomes in both cases were composed of phosphatidyl choline, phosphatidyl serine, and cholesterol in the ratio 5:1:5.
[b]Size I was extruded to yield approximately 1.2 micron liposomes. Size II was extruded to yield approximately 0.5 micron liposomes.

Table 5 shows that size I liposomes accumulate in lung tissue; whereas no difference with respect to spleen tissue is noted. At early times, size II liposomes, on the other hand, preferentially accumulate in liver tissue.

Reaction with DNA

Measurements have been made with respect to the bis-anthracyclines' ability to react with DNA. Receptor dissociation time has been measured by stopped flow spectrophotometry. Such measurements indicate that mono-anthracyclines dissociate from double-stranded DNA in substantially under one second; however bis-anthracyclines dissociation times from double-stranded DNA is 20 to 100 fold longer.

What is claimed is:

1. As compositions of matter, bis-anthracycline compounds wherein two anthracycline moieties are linked through their respective C-13 carbon atoms by a cross-linking substituent, said cross-linking substituent being hydroxy-dicarboxylic acid hydrazones or amino-dicarboxylic acid hydrazones.

2. The compounds of claim 1, wherein both of said anthracycline moieties are either daunorubicin or adriamycin.

3. As compositions of matter, bis-anthracycline compounds wherein two anthracycline moities are linked through their respective C-14 carbon atoms by a cross-linking substituent, said cross-linking substituent being hydroxy-dicarboxylic acid hydrazones or amino-dicarboxylic acid hydrazones.

4. The compositions of claim 1 or 3 wherein the anthracycline moieties are linked by the substituent

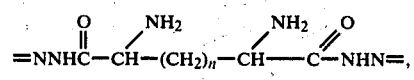

wherein n=1 to 6.

5. The compositions of claim 1 wherein said cross-linking substituent is

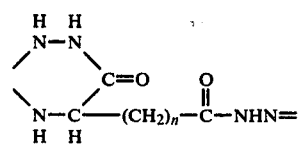

wherein n=1 to 6.

6. The compounds:

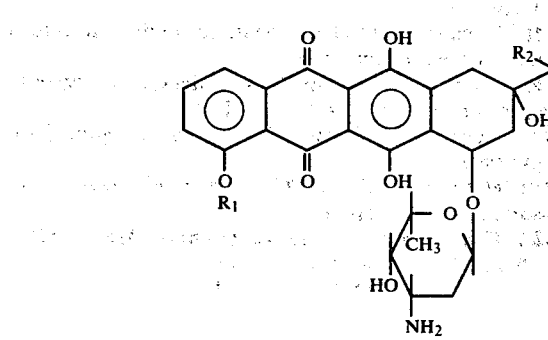
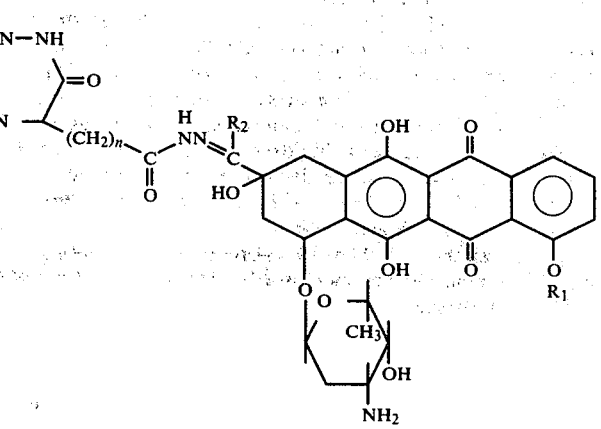

wherein n=1 to 6 and $R_1$ is H or $CH_3$, and $R_2$ is $CH_3$ or $CH_2OH$.

7. The bis-anthracyclines of claim 1 wherein said bis-anthracyclines are in the pharmacologically acceptable addition salt form.

8. The compounds:

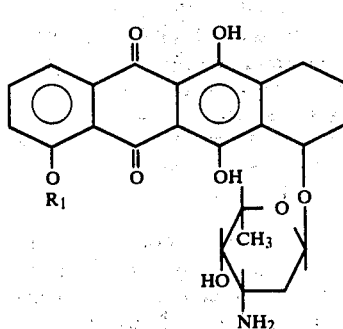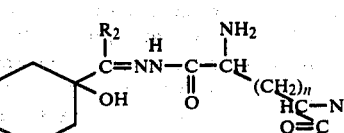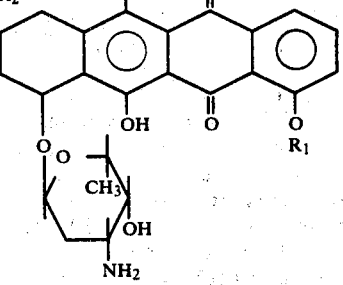

wherein n=1 to 4 and $R_1$ is H or $CH_3$, and $R_2$ is $CH_3$ or $CH_2OH$.

9. The bis-anthracycline compound:

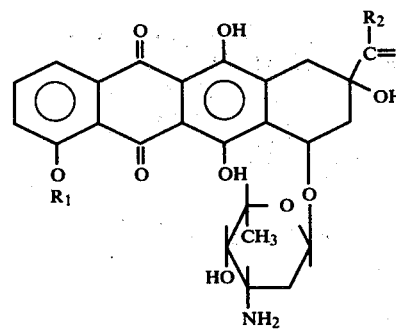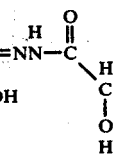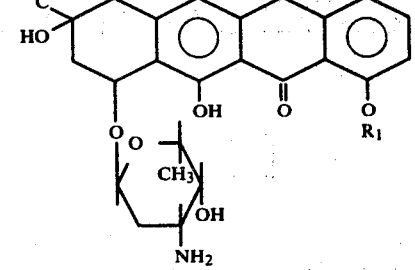

wherein $R_1$ is H or $CH_3$; $R_2$ is $CH_3$ or $CH_2OH$ or; and $R_3$ is H or OH and n=0 to 3.

10. The bis-anthracyclines of claim 1 in the alpha-, beta-, or alpha-beta, isomeric forms.

11. A method of producing bis-anthracycline compounds comprising reacting anthracyclines in a solvent medium with a cross-linking agent in the presence of an acid at slightly elevated temperatures, said cross-linking agent being hydroxy-dicarboxylic acid dihydrizades or amino-dicarboxylic acid dihydrizides, for a period of time sufficient to produce the bis-anthracycline compounds, and recovering the bis-anthracycline compounds from the reactant solution.

12. The method of claim 11 wherein the cross-linking agent is a reaction product of a hydroxy-dicarboxylic acid and hydrazine.

13. The method of claim 11 wherein the cross-linking agent is a reaction product of an amino-dicarboxylic acid and hydrazine.

14. The method as in claim 11 wherein the cross-linking agent is a reaction product of amino-diesters and hydrazine.

15. The method of claim 11 wherein the reaction takes place at a temperature of about 25° C.

16. The method of claim 11 wherein a strong organic acid is added to the reaction medium.

17. The method of claim 16 wherein the organic acid is acetic acid.

18. The method of claim 11 wherein a mineral acid is added to the reaction medium.

19. The method of claim 11 wherein a strong organic base is added to the reaction medium.

20. The method of claim 19 wherein the organic base is pyridine.

21. The method of claim 11 wherein an inorganic base is added to the reaction medium.

22. The bis-anthracycline compounds of claim 1, 2, 3, 6, 7, 8 or 9 incorporated into liposomes.

* * * * *

UNITED STATES PATENT AND TRADEMARK OFFICE
CERTIFICATE OF CORRECTION

PATENT NO. : 4,263,428

DATED : April 21, 1981

INVENTOR(S) : Martin A. Apple et al.

It is certified that error appears in the above—identified patent and that said Letters Patent is hereby corrected as shown below:

Column 16, line 40, "phasse" should read -- phase --.

Columns 9 and 10 in the uppermost straight chain linked bis-daunorubicin molecular structure in the right hand anthracycline in the quinone the structure 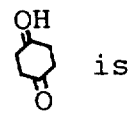 is printed incorrectly. It should be: 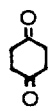

UNITED STATES PATENT OFFICE
CERTIFICATE OF CORRECTION

Patent No. 4,263,428　　　　　　　　　Dated April 21, 1981

Inventor(s) Martin A. Apple et al.

It is certified that error appears in the above-identified patent and that said Letters Patent are hereby corrected as shown below:

Columns 13 and 14, at very bottom the word "pyridine" should be printed alongside the arrow, thus:

$$\Big\downarrow \text{pyridine}$$

Signed and Sealed this

Fifteenth Day of September 1981

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,263,428
DATED : April 21, 1981
INVENTOR(S) : Martin A. Apple et al.

It is certified that error appears in the above—identified patent and that said Letters Patent is hereby corrected as shown below:

Column 1, line 9 insert:

The invention described herein was made in the course of work under a grant or award from the Department of Health and Human Services.

Signed and Sealed this

Eighth Day of June 1982

[SEAL]

Attest:

GERALD J. MOSSINGHOFF

*Attesting Officer*  *Commissioner of Patents and Trademarks*